(12) United States Patent
Popplewell et al.

(10) Patent No.: US 9,347,023 B2
(45) Date of Patent: May 24, 2016

(54) DISPERSED CAPSULES IN LYOTROPIC OR LYOTROPIC LIQUID CRYSTAL SURFACTANT PHASES FOR ENHANCED CAPSULE DEPOSITION

(71) Applicants: Lewis Michael Popplewell, Morganville, NJ (US); Johan G. L. Pluyter, Middletown, NJ (US); Judith Kerschner, Hawthorne, NJ (US); Timothy Young, Middletown, NJ (US); Takashi Sasaki, Matawan, NJ (US)

(72) Inventors: Lewis Michael Popplewell, Morganville, NJ (US); Johan G. L. Pluyter, Middletown, NJ (US); Judith Kerschner, Hawthorne, NJ (US); Timothy Young, Middletown, NJ (US); Takashi Sasaki, Matawan, NJ (US)

( * ) Notice: Subject to any disclaimer, the term of this patent is extended or adjusted under 35 U.S.C. 154(b) by 0 days.

(21) Appl. No.: 14/647,754

(22) PCT Filed: Nov. 25, 2013

(86) PCT No.: PCT/US2013/071579
§ 371 (c)(1),
(2) Date: May 27, 2015

(87) PCT Pub. No.: WO2014/085286
PCT Pub. Date: Jun. 5, 2014

(65) Prior Publication Data
US 2015/0291910 A1    Oct. 15, 2015

Related U.S. Application Data

(60) Provisional application No. 61/730,246, filed on Nov. 27, 2012.

(51) Int. Cl.
| | | |
|---|---|---|
| A61L 9/04 | (2006.01) | |
| C11D 3/50 | (2006.01) | |
| C11B 9/00 | (2006.01) | |
| A61K 8/39 | (2006.01) | |
| A61K 8/41 | (2006.01) | |
| A61K 8/46 | (2006.01) | |
| A61Q 5/02 | (2006.01) | |
| A61Q 5/12 | (2006.01) | |
| A61Q 13/00 | (2006.01) | |
| A61K 8/84 | (2006.01) | |
| A61Q 19/10 | (2006.01) | |
| A61K 8/92 | (2006.01) | |
| A61K 8/02 | (2006.01) | |
| A61K 8/11 | (2006.01) | |

(52) U.S. Cl.
CPC .............. *C11B 9/00* (2013.01); *A61K 8/0295* (2013.01); *A61K 8/11* (2013.01); *A61K 8/39* (2013.01); *A61K 8/416* (2013.01); *A61K 8/466* (2013.01); *A61K 8/84* (2013.01); *A61K 8/92* (2013.01); *A61Q 5/02* (2013.01); *A61Q 5/12* (2013.01); *A61Q 13/00* (2013.01); *A61Q 19/10* (2013.01); *A61K 2800/56* (2013.01)

(58) Field of Classification Search
CPC ........................................... C11B 9/00
USPC ......................................... 512/4, 1
See application file for complete search history.

(56) References Cited

U.S. PATENT DOCUMENTS

| | | | | |
|---|---|---|---|---|
| 2008/0146478 A1* | 6/2008 | Lei | ............ | A61K 8/11 510/119 |
| 2011/0269657 A1* | 11/2011 | Dihora | ............ | A61K 8/11 510/119 |
| 2011/0308556 A1* | 12/2011 | Smets | ............ | A61K 8/738 134/26 |

* cited by examiner

Primary Examiner — Ling-Siu Choi
Assistant Examiner — Jessica E Whiteley
(74) Attorney, Agent, or Firm — Martin Zhang; XuFan Tseng; Elizabeth M. Quirk

(57) ABSTRACT

The present invention is a fragrance containing capsule composition dispersed into a lyotropic liquid crystalline surfactant phase as well as a consumer product base containing the same.

36 Claims, 2 Drawing Sheets

DISPERSED CAPSULES IN LYOTROPIC OR LYOTROPIC LIQUID CRYSTAL SURFACTANT PHASES FOR ENHANCED CAPSULE DEPOSITION

CROSS REFERENCE TO RELATED APPLICATIONS

This application is the national stage entry under 35 U.S.C. 371 for PCT/US2013/071579, filed on Nov. 25, 2013, which claims the benefit of priority from U.S. Provisional Application Ser. No. 61/730,246, filed Nov. 27, 2012. The contents of both applications are incorporated herein by reference in their entirety.

BACKGROUND

A difficulty encountered with using encapsulated fragrances in personal rinse-off compositions (i.e., body wash, conditioner, shampoo) is that the fragrance capsules are difficult to deposit onto skin and hair due to strong interactions with the product surfactants. These surfactants remove particulates from surfaces and keep the particulates for adhering (soil anti-redeposition) but the surfactants can also alter the surface of fragrance capsules. Previous work has shown that polymers can be added to the capsules and consumer products to enhance deposition on a variety of surfaces. However, the extent of deposition enhancement is affected by the presence of surfactants and the types of surfactants used in personal care products.

SUMMARY OF THE INVENTION

The present invention describes the use fragrance containing capsules that are dispersed into lyotropic liquid crystalline surfactant phases. It has been surprisingly found that when fragrance containing capsules are dispersed into lyotropic liquid crystalline surfactant phases before being dispersed into a consumer product, the level of performance is significantly enhanced versus dispersing the capsules on their own. Thus, this invention is a composition composed of fragrance containing capsules dispersed into a lyotropic liquid crystalline surfactant phase and consumer products containing the same.

In one embodiment, the surfactant phase is an oil-continuous liquid crystalline phase. In accordance with this embodiment, the oil-continuous liquid crystalline phase can include an anionic surfactant (e.g., a sodium dioctylsulfosuccinate, sodium ditridecylsulfosuccinate, sodium didecylsulfosuccinate, sodium bis-tridecyl sulfosuccinate, sodium benzene alkyl sulphonate, or blends thereof) and cationic surfactant (e.g., dioleoyl ammonium methosulfate, methyl bis(hydrogenated tallow amidoethyl)-2-hydroxyethyl ammonium methyl sulfate, methyl bis(tallow amidoethyl)-2-hydroxyethyl ammonium methyl sulfate, methyl bis(soya amidoethyl)-2-hydroxyethyl ammonium methyl sulfate, methyl bis(canola amidoethyl)-2-hydroxyethyl ammonium methyl sulfate, methyl bis(tallowamido ethyl)-2-tallow imidazolinium methyl sulfate, dioleoyl ammonium methosulfate, dipalmityl ammonium methosulfate, or blends thereof). In specific embodiments, the oil-continuous liquid crystalline phase is prepared with sodium bis-tridecyl sulphosuccinate and dioleoyl ammonium methosulfate; sodium dioctyl sulfosuccinate and methyl bis(Soya amidoethyl)hydroxyethyl ammonium methyl sulfate; or sodium dioctyl sulfosuccinate and dipalmityl ammonium methosulfate.

Capsules of this invention include microcapsules, microparticles, nanoparticles, liposomes, vesicles, or spores. In some embodiments, microcapsules can be composed of urea-formaldehyde, melamine-formaldehyde, phenolic-formaldehyde, urea-glutaraldehyde, melamine-glutaraldehyde, phenolic-glutaraldehyde, or combinations thereof; polyurea, polyurethane, or a combination thereof; acrylate-based hydrogel core-shell capsules or polyurea/polyurethane-acrylic hybrid core-shell capsules; polyamide and polyester-based capsules; or silica or silica-derived materials. In some embodiments, the microcapsules are physically or chemically coated with a polymer that facilitates incorporation of the microcapsules into the surfactant phase. In further embodiments, the microcapsules or nanoparticles are composed of polyethylene, poly vinyl acetate, ethylene-vinyl acetate copolymers, polyacrylates such as copolymers of methyl methacrylate, polyurethanes, polyureas, formaldehyde resins, polyesters or polyamide. In yet other embodiments, the spores are plant spores loaded with a fragrance, and optionally sealed with polymers, and the vesicles are polymersomes.

DETAILED DESCRIPTION OF THE INVENTION

Figure 1:
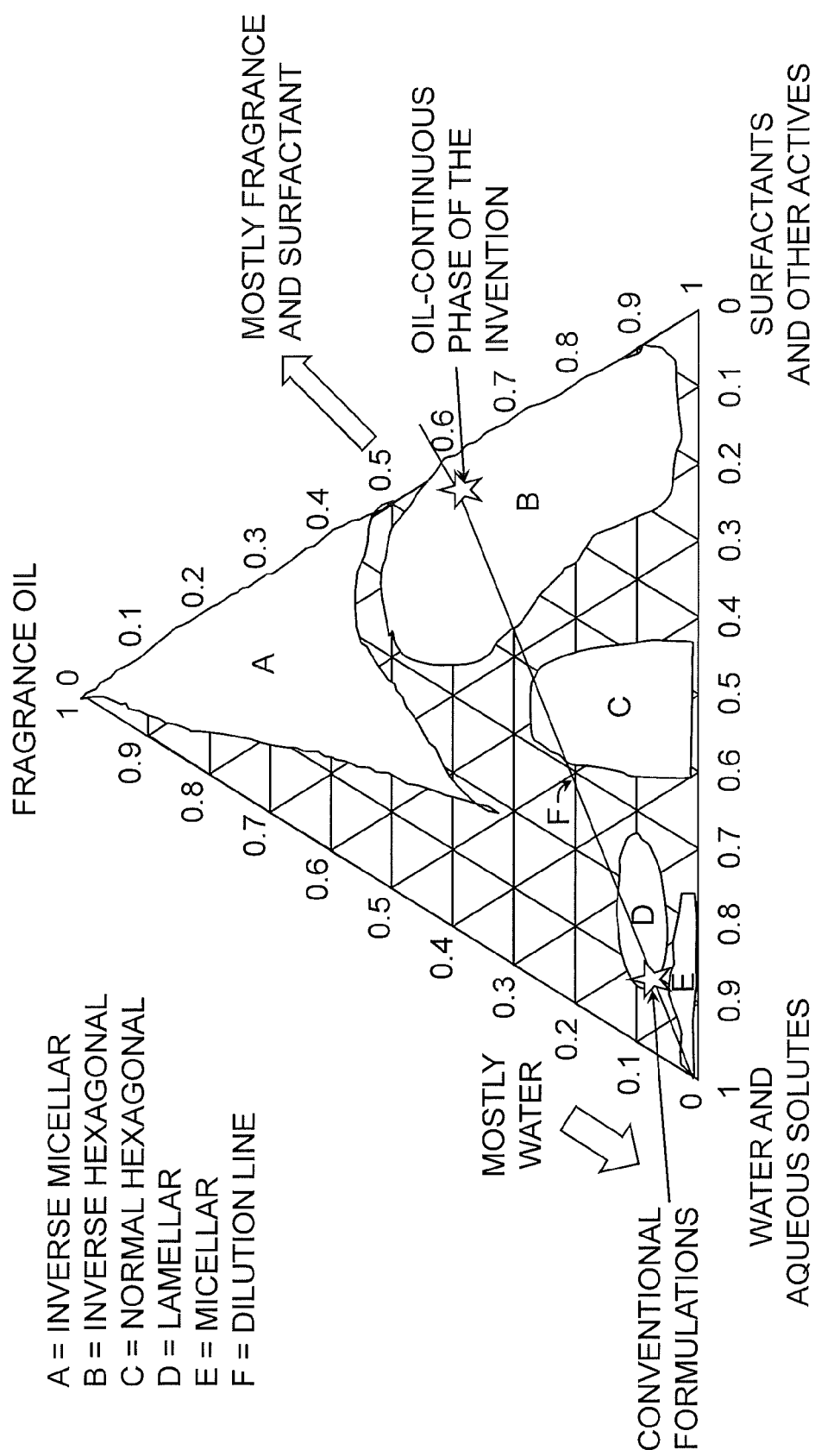
FIG. 1 shows a phase diagram of the formulation of the invention.

It has now been found that the deposition of fragrance capsules onto hair or skin can be enhanced by dispersing these fragrance containing capsules into lyotropic liquid crystalline surfactant phases before being dispersed into the consumer product. Advantageously, the lyotropic liquid crystalline phase alters the surface of the capsules thereby minimizing alterations of the capsule surface when the capsules are added to an existing consumer product formulation. This approach not only takes advantage of electrostatic and hydrogen/dipole interactions but also viscous/tacky adhesive forces. Therefore, the present invention is a composition of fragrance containing capsules dispersed into a lyotropic liquid crystalline surfactant phase and consumer products containing the same.

For the purposes of this invention, the term "capsules" is intended to include microcapsules, microparticles, nanoparticles, liposomes, vesicles, and spores. As known in the art and used herein, microcapsules, microparticles and nanoparticles refers to particles, which are typically solid and contain the fragrance to be delivered within the core of the particle or capsule. Microparticles (or microcapsules) and nanoparticles generally differ in size. Microparticles and microcapsules typically have a size range of about 1 to about 1000 microns. Nanoparticles typically have a particle size range of about 10 to about 1000 nm.

Any permeable capsule wall material can be used in the preparation of the microcapsules, microparticles or nanoparticles of this invention. Suitable wall materials include, but are not limited to friable wall materials such as urea-formaldehyde, melamine-formaldehyde, phenolic-formaldehyde, urea-glutaraldehyde, melamine-glutaraldehyde, phenolic-glutaraldehyde, or combinations thereof; or polyurea, polyurethane, or a combination thereof. In addition, the microcapsules can be acrylate-based hydrogel core-shell capsules or polyurea/polyurethane-acrylic hybrid core-shell capsules. Furthermore, the microcapsules can be polyamide- and polyester-based capsules. Moreover, silica or silica-derived materials, which are typically prepared via sol-gel processes, can be used in the preparation of microcapsules of this invention (see, e.g., US 2010/0143422). Capsules having shell walls composed of polyolefin, polysaccharide, protein, lipid, modified cellulose, gums, polyphosphate, polystyrene, and polyesters or combinations of these materials are also functional.

Suitable polymers for encapsulation in the present invention include amino-based prepolymers such as urea-, melamine-, benzoguanamine-, and glycouril-formaldehyde resins and dimethyloldihydroxyethylene urea type prepolymers. These prepolymers can be used as blends and cross linkers with polyvinyl alcohol, polyvinyl amines, acrylates (acid functionality preferred), amines, polysaccharides, polyureas/urethanes, poly amino acids, and proteins. Other suitable polymers include polyesters, including biodegradable polyesters, polyamides, polyacrylates and polyacrylamides, polyvinyl polymer and copolymers with polyacrylates, polyurethanes, polyethers, polyureas, polycarbonates, naturally occurring polymers such as, polyanhydrides, polyphosphazines, polyoxazolines, and UV-cured polyolefins.

The present invention also contemplates the use of UV-cured versions of all the above polymer materials, epoxy-cross linked polyalcohols, polyamines, and polyurethanes/ureas, as well as multiple shell versions of the above.

As indicated, the microcapsules of this invention can be friable. Friability refers to the propensity of the capsules to rupture or break open when subjected to direct external pressures or shear forces. For the purposes of this invention, a capsule is "friable" if, while attached to a treated surface (e.g., a fabric), the microcapsule can be ruptured by the forces encountered when the microcapsule-containing surface is manipulated, e.g., by being worn, handled or ironed thereby releasing the contents of the microcapsule.

Friable shell-core microcapsules can be prepared by methods such as interfacial polymerization and polycondensation. See, e.g., U.S. Pat. Nos. 3,516,941, 4,520,142, 4,528,226, 4,681,806, 4,145,184; GB 2,073,132; WO 99/17871; and *Microencapsulation: Methods and Industrial Applications*, Edited by Benita and Simon (Marcel Dekker, Inc. 1996). It is recognized that many variations with regard to materials and process steps are possible, however, non-limiting examples of friable shell materials suitable for making a friable shell of the microcapsule of this invention include urea-formaldehyde, melamine-formaldehyde, phenol-formaldehyde, amido-aldehyde, gelatin, gelatin/gum arabic blend, polyurethane, polyamides, or combinations thereof.

Methods for preparing capsules with urea formaldehyde, urea aldehyde, or amido-aldehyde are disclosed in, e.g., U.S. Pat. No. 5,204,185, EP 0 443 428 A2, U.S. Pat. No. 3,516,941 and EP 0 158 449 A1. Polyurea and polyurethane microcapsules are known in art for use in the encapsulation of agrochemicals, e.g., herbicides and pesticides (see, e.g., U.S. Pat. No. 6,133,197) and for the release of benefit agents intended for laundry, washing, cleaning, surface care and personal and skin care (see, e.g., US Patent Application 2012/0148644). In some embodiments, the microcapsules of this invention are physically or chemically coated with a polymer to facilitate incorporation into the surfactant phase. Preferably the polymer is water soluble and is nonionic, anionic, cationic, or amphoteric. Those skilled in the art would appreciate that the charge of these polymers can be adjusted by changing the pH, depending on the product in which this technology is to be used. Any suitable method for coating the polymer onto the fragrance containing microcapsule can be used. The nature of suitable polymers for assisted capsule delivery to interfaces depends on the compatibility with the capsule wall chemistry since there has to be some association to the capsule wall. This association can be through physical interactions, such as hydrogen bonding, ionic interactions, hydrophobic interactions, electron transfer interactions or, alternatively, the polymer coating could be chemically (covalently) grafted to the capsule or particle surface. Chemical modification of the capsule surface is another way to optimize anchoring of the polymer coating to capsule surface. Furthermore, the capsule and the polymer need to want to go to the desired interface and, therefore, need to be compatible with the chemistry (polarity, for instance) of that interface. Therefore, depending on which capsule chemistry and interface (e.g., cotton, polyester, hair, skin, wool) is used, the polymer can be selected from one or more polymers with an overall zero (amphoteric: mixture of cationic and anionic functional groups) or net positive charge, based on the following polymer backbones: polysaccharides, polypeptides, polycarbonates, polyesters, polyolefinic (vinyl, acrylic, acrylamide, poly diene), polyester, polyether, polyurethane, polyoxazoline, polyamine, silicone, polyphosphazine, olyaromatic, poly heterocyclic, or polyionene, with molecular weight (MW) ranging from about 1,000 to about 1000,000,000, preferably from about 5,000 to about 10,000,000. As used herein, molecular weight is provided as weight average molecular weight. Optionally, these cationic polymers can be used in combination with nonionic and anionic polymers and surfactants, possibly through coacervate formation. A more detailed list of cationic polymers that can be used to coat the encapsulated fragrance is provided in U.S. Pat. Nos. 7,119,057 and 7,122,512.

In certain embodiments, the microcapsules or nanoparticles are prepared with polyethylene, poly vinyl acetate, ethylene-vinyl acetate copolymers, a polyacrylate such as a copolymer of methyl methacrylate, polyurethane, polyurea, formaldehyde resin, polyester, or polyamide.

Liposomes or vesicles are microscopic spheres having a core surrounded by one or more outer layers made up of lipids arranged in a bi-layer configuration (see, generally, Chonn, et al. (1995) *Curr. Opin. Biotech.* 6:698-708). As known in the art, liposomes can be categorized into various types: multilamellar (MLV), stable plurilamellar (SPLV), small unilamellar (SUV) or large unilamellar (LUV) vesicles. Liposomes can be prepared from various lipid compounds, which may be synthetic or naturally occurring, including phosphatidyl ethers and esters, such as phosphotidylserine, phosphotidylcholine, phosphatidyl ethanolamine, phosphatidylinositol, dimyristoylphosphatidylcholine; steroids such as cholesterol; sphingomyelin; glycerolipids; and other lipids. See, for example, U.S. Pat. No. 5,833,948.

This invention also includes the use of vesicles, i.e., small enclosed sacs having a bimolecular membrane structure. In some embodiments, the vesicle is a polymersome. A polymersome is vesicle composed of block copolymers that include a hydrophobic block and a hydrophilic block. These block copolymers may have a number average molecular weight in the range of from about 2,000 to about 100,000. The hydrophilic block of the block copolymers may include any polymer for which water is a good solvent. Examples of suitable polymers for the hydrophilic block include, but are not limited to, poly(acrylic acid), poly(ethylene oxide), poly(methacrylic acid), poly(2-acrylamido, 2-methyl propane sulfonic acid), poly(acrylamide), and poly(2-dimethylaminoethyl methacrylate). The hydrophobic block may include any polymer for which water is not a good solvent. Examples of suitable hydrophobic polymers for the hydrophobic block include, but are not limited to, poly(butadiene), poly(styrene), poly(isoprene), poly(ethylene), poly(ethylene propylene), and poly(ethylene butene). The polymersomes of this invention may be prepared from block copolymers by any process, including, but not limited to, film rehydration, electroformation, and solvent injection. Exemplary processes and materials for preparation of polymersomes are described by Discher & Eisenberg (2002) *Science* 297:967-73; US 2012/0231055; PCT/NL2006/000052; U.S. Pat. No. 7,151,077; US 2008/0181939; and US 2005/0003016.

Another capsule of this invention is a spore or pollen grain from a plant or fungus. As is known in the art, pollen grains can be modified by removing their natural contents and substituting or loading the core with a variety of materials including drugs, chemicals and other pharmacologically active substances. See U.S. Pat. No. 5,013,552. To modify solubility, the spore can be coated or sealed with a polymer, e.g., a film-forming material composed of plasticizers, extenders, fillers, and other common excipients. By "film-forming" is meant the property of forming a solid film, coating or layer at ambient or room temperatures. If the film-forming material is thermoplastic or capable of being melted or liquified at elevated temperatures, it may be applied to the spore or underlying layer of active substance by spray, immersion, or other means of deposition. Examples of film-forming materials include, but are not limited to, polymethylsiloxane, polyacrylamide, polyvinyl pyrrolidone (PVP), polyvinyl alcohol, ethylene/vinyl acetate copolymer, polyesters, polyurethanes, polycarbonates, polystyrene, polymethyl methacrylate, polyvinyl acetate, polyols, polythiols, polyamines, polyethylene, polypropylene, cellulosics such as regenerated cellulose, ethyl cellulose, cellulose acetate butyrate (CAB), fats, waxes, etc. See U.S. Pat. No. 5,275,819.

Encapsulated within the core of the capsules of the invention is one or more fragrance oils. As referred to herein, the term "fragrance oil" refers to perfume materials and may include single perfume raw materials or blends of oils. A wide variety of chemicals may be employed as or included in the fragrance oil, including materials such as aldehydes and alcohols, as well as some esters and ketones and lactones of high polarity. More commonly, naturally occurring plant and animal oils and exudates including complex mixtures of various chemical components are known for use as or inclusion in Fragrance Oils.

Examples of fragrance oils useful herein include, but are not limited to, animal fragrances such as musk oil, civet, castoreum, ambergris, plant fragrances such as nutmeg extract, cardamom extract, ginger extract, cinnamon extract, patchouli oil, geranium oil, orange oil, mandarin oil, orange flower extract, cedarwood, vetyver, lavandin, ylang extract, tuberose extract, sandalwood oil, bergamot oil, rosemary oil, spearmint oil, peppermint oil, lemon oil, lavender oil, citronella oil, chamomile oil, clove oil, sage oil, neroli oil, labdanum oil, eucalyptus oil, verbena oil, mimosa extract, narcissus extract, carrot seed extract, jasmine extract, olibanum extract, rose extract and mixtures thereof.

Other examples of suitable fragrance oils include, but are not limited to, chemical substances such as acetophenone, adoxal, aldehyde C-12, aldehyde C-14, aldehyde C-18, allyl caprylate, ambroxan, amyl acetate, dimethylindane derivatives, α-amylcinnamic aldehyde, anethole, anisaldehyde, benzaldehyde, benzyl acetate, benzyl alcohol and ester derivatives, benzyl propionate, benzyl salicylate, borneol, butyl acetate, camphor, carbitol, cinnamaldehyde, cinnamyl acetate, cinnamyl alcohol, cis-3-hexanol and ester derivatives, cis-3-hexenyl methyl carbonate, citral, citronellol and ester derivatives, cumin aldehyde, cyclamen aldehyde, cyclo galbanate, damascones, decalactone, decanol, estragole, dihydromyrcenol, dimethyl benzyl carbinol, 6,8-dimethyl-2-nonanol, dimethyl benzyl carbinyl butyrate, ethyl acetate, ethyl isobutyrate, ethyl butyrate, ethyl propionate, ethyl caprylate, ethyl cinnamate, ethyl hexanoate, ethyl valerate, ethyl vanillin, eugenol, exaltolide, fenchone, fruity esters such as ethyl 2-methyl butyrate, galaxolide, geraniol and ester derivatives, helional, 2-heptonone, hexenol, α-hexylcinnamic aldehyde, hydroxycitronellal, indole, isoamyl acetate, isoeugenol acetate, ionones, isoeugenol, isoamyl iso-valerate, iso E super, limonene, linalool, lilial, linalyl acetate, lyral, majantol, mayol, melonal, menthol, p-methylacetophenone, methyl anthranilate, methyl cedrylone, methyl dihydrojasmonate, methyl eugenol, methyl ionone, methyl-β-naphthyl ketone, methylphenylcarbinyl acetate, mugetanol, γ-nonalactone, octanal, phenyl ethyl acetate, phenyl-acetaldehyde dimethyl acetate, phenoxyethyl isobutyrate, phenyl ethyl alcohol, pinenes, sandalore, santalol, stemone, thymol, terpenes, triplal, triethyl citrate, 3,3,5-trimethylcyclohexanol, γ-undecalactone, undecenal, vanillin, veloutone, verdox and mixtures thereof.

Suitable fragrance oils can be found in U.S. Pat. Nos. 4,145,184, 4,209,417, 4,515,705, and 4,152,272, all of which are incorporated herein by reference.

As indicated, deposition of fragrance capsules onto surfaces can be enhanced by dispersing the fragrance containing capsules into lyotropic liquid crystalline surfactant phases before being dispersed into the consumer product. In one embodiment, the capsule is dispersed in a lyotropic liquid crystalline phase, such as a cubic, hexagonal and inverse hexagonal phase. In accordance with particular aspects of this embodiment, the lyotropic liquid crystalline surfactant phase is an oil-continuous liquid crystalline phase.

The liquid crystalline phase of the invention is formed by combining the fragrance containing capsule with low Hydrophilic-lipophilic balance (HLB), water insoluble surfactants to obtain a phase which is oil-continuous or bicontinuous rather than water continuous, wherein the phases do not extend from the micellar phase (FIG. 1). The phases of this invention extend from the "inverse micellar" (water cores in oil media, rather than the reverse). Some do and some do not rotate plane polarized light. Using the present formulation, two or more additional phases to the micellar phase can occur. The continuous phase can be determined experimentally by testing the conductivity with a conductivity meter or using an impedance analyzer.

In general, the liquid crystalline phase of the invention is prepared by combining one or more cationic surfactant(s) and one or more anionic surfactant(s) with the fragrance containing capsules. The composition of the invention may include from about 20% wt to about 70% wt surfactant, preferably from about 30% wt to about 60% wt, more preferably from about 30% wt to about 45% wt, even more preferably from about 35% wt to about 45% wt, more preferably still from about 40% wt.

Anionic surfactants which may be used in this invention include alkyl sulfates, alkyl ether sulfates, sulfated monoglycerides, sulfonated olefins, alkyl aryl sulfonates, primary or secondary alkane sulfonates, alkyl sulfosuccinates, acyl taurates, acyl isethionates, alkyl glycerylether sulfonate, sulfonated methyl esters, sulfonated fatty acids, alkyl phosphates, acyl glutamates, acyl sarcosinates, alkyl sulfoacetates, acylated peptides, alkyl ether carboxylates, acyl lactylates, and combinations thereof. In some embodiments, the anionic surfactant is a sulfosuccinate or sulfate. Sulfosuccinates include, but are not limited to the dialkylsulfosuccinates such as sodium dioctylsulfosuccinate, sodium ditridecylsulfosuccinate, sodium didecylsulfosuccinate, sodium bis-tridecyl sulfosuccinate, or blends thereof. In particular embodiments, the anionic surfactant is sodium bis-tridecyl sulfosuccinate or sodium dioctyl sulfosuccinate. Sulphonates of use in this invention, include, but are not limited to sodium benzene alkyl sulphonate.

The formulation according to the invention may include from about 1% wt to about 70% wt anionic surfactant, preferably from about 1% wt to about 60% wt, more preferably from about 10% wt to about 50% wt, even more preferably from about 10% wt to about 45% wt, more preferably still from about 15% to about 50% wt.

Cationic surfactants which may be employed according to the invention include, e.g., fatty amines, di-fatty quaternary amines, trifatty quaternary amines, imidazolinium quaternary amines, and combinations thereof. Suitable cationic surfactants are particularly cetyl trimethyl ammonium chloride, palmitamidopropyltrimonum chloride, dipalmitoyltrimonium chloride, distearyldimonium chloride, dipalmitoylethylhydroxyethylmonium chloride, dioleoylethyl ammonium methosulfate, dioleoylethyl hydroxyethylmonium methosulfate, dilinolamidopropyldimonium chloride, dioleylethyl hydroxyethylmonium chloride, dipalmitoylethyldimonium chloride and or didodecyl dimethyl ammonium chloride. In particular embodiments, the cationic surfactant is dioleoyl ammonium methosulfate. In other embodiments, the cationic surfactant is methyl bis(hydrogenated tallow amidoethyl)-2-hydroxyethyl ammonium methyl sulfate, methyl bis(tallow amidoethyl)-2-hydroxyethyl ammonium methyl sulfate, methyl bis(soya amidoethyl)-2-hydroxyethyl ammonium methyl sulfate, methyl bis(canola amidoethyl)-2-hydroxyethyl ammonium methyl sulfate, methyl bis(tallowamido ethyl)-2-tallow imidazolinium methyl sulfate, dioleoyl ammonium methosulfate, or didodecyl dimethyl ammonium chloride, dipalmityl ammonium methosulfate, or blends thereof.

The formulation according to the invention may include from about 1% wt to about 30% wt cationic surfactant, preferably from about 5% wt to about 30% wt, more preferably from about 10% wt to about 25% wt, even more preferably from about 12% wt to about 25% wt.

As mentioned, the surfactant of the formulation of this invention advantageously includes both anionic and cationic surfactants. With anionic-cationic binary surfactant systems, oil continuous phases occur upon addition of water and oil. These depend strongly on surfactant ratio, which are experimentally determined. However, total surfactant and oil ratios are the same as for single surfactant systems.

The ratio of a lyotropic liquid crystalline surfactant phase to capsule dispersion is desirably in the range from about 99:1 to about 10:90, preferably in the range from about 99:1 to about 25:75, more preferred in the range from about 99:1 to about 40:60.

In certain embodiments, the formulation of this invention also includes an aqueous component such as water. Typically, the aqueous component is from about 0% wt to about 30% wt of the formulation, preferably from about 10% wt to about 30% wt, more preferably from about 15% wt to about 30% wt, even more preferably from about 20% wt to about 25% wt.

In some embodiments, the fragrance containing capsule is dispersed into a concentrated lyotropic liquid crystalline phase prior to introduction of the same into a consumer product. In another embodiment, a non-organized surfactant phase is combined with a fragrance containing capsule, wherein upon addition of the mixture to a consumer product such as a shampoo or conditioner, a lyotropic liquid crystalline surfactant phase with embedded capsules is formed via the water in the consumer product. In an alternative embodiment, the surfactant phase may be created using the water phase in the capsule dispersion such that the water phase of the dispersion is a low viscosity microemulsion. When this dispersion is added to the consumer product at particular levels, the desired viscous/dense/organized phases are formed with the capsules embedded therein. The advantage of this approach is that the dispersion can be delivered as a one-stop solution with manageable viscous properties.

In a further embodiment, cationic or amphoteric polymers or blends of cationic and anionic and amphoteric polymers are added to the consumer product base that contains the dispersed viscous/dense/organized capsule-containing phases in order to further enhance deposition of the dense phase/capsules particulates. Polymers of use in this embodiment include, but are not limited to those disclosed in U.S. Pat. Nos. 7,119,057, 7,632,789, US 2012/0093899 A1 and US 2012/0148644A1. Substantivity of these polymers may be further improved through formulation with cationic, amphoteric and nonionic surfactants and emulsifiers, or by coacervate formation between surfactants and polymers or between different polymers. Combinations of polymeric systems (including those mentioned previously) may be used for this purpose as well as those disclosed in EP 1995/000400185. Furthermore, polymerization of the monomers listed above into a block, graft or star (with various arms) polymers can often increase the substantivity toward various surfaces. The monomers in the various blocks, graft and arms can be selected from the various polymer classes listed in this specification.

The preferred cationically charged materials include cationically modified starch and cationically modified guar, polymers comprising poly diallyl dimethyl ammonium halides (PolyDADMAC), and copolymers of DADMAC with vinyl pyrrolidone, acrylamides, imidazoles, imidazolinium halides, and the like. For instance, Polyquaternium-6, 7, 22 and 39, all available from Ondeo Nalco. Another set of preferred cationic polymers are those composed using the MAP-TAC cationic monomer like MERQUAT 2001 and MERQUAT 2003PR and MAQUAT PQ125. A further preferred set of polymers are combinations of cationic polymers (containing quarternary monomers like DADMAC and MAPTAC) and polyamines like poly vinyl amine derivatives and polyethylene imine derivatives.

A preferred cationic starch has a molecular weight of from about 100,000 to about 500,000,000, preferably from about 200,000 to about 10,000,000 and most preferably from about 250,000 to about 5,000,000. The preferred cationic starch products are HI-CAT CWS42 and HI-CAT 02 and are commercially available from ROQUETTE AMERICA, Inc.

A preferred cationic guar has a molecular weight of from about 50,000 to about 5,000,000. The preferred cationic guar products are Jaguar C-162 and Jaguar C-17 and are commercially available from Rhodia Inc.

The level of cationic polymer is from about 1% to about 3000%, preferably from about 5% to about 1000% and most preferably from about 10% to about 500% of the fragrance containing compositions, based on a ratio with the fragrance on a dry basis.

When the capsule and crystalline phase structure is re-dispersed into surfactant containing bases, like fabric softener, shower gels, shampoos and liquid detergents, the capsule and crystalline phase is expected to retain its structure so that is not completely dissolved or solubilized in the product base. When the product is used, in a wash, rinse application, the fragrance capsule that are tied up in the liquid crystal or semi-solid phase are expected to deposit onto skin, hair, fabric or other surfaces. This effect causes the fragranced capsules to occur at higher levels on skin, fabric hair, etc. following a wash or rinse procedure thereby allowing for possible higher deposition and substantivity of fragranced capsules that a consumer may notice and appreciate.

Accordingly, the composition of this invention finds particular use in the consumer product bases, e.g., fabric care products, including detergents, fabric conditioners, and the like; as well as personal care products which include shampoos, body wash, conditioners, hair rinses, hair refreshers, body washes, soaps, anti-perspirants, deodorants and the like. These products are well known in the art. For example, fabric softener systems are described in U.S. Pat. Nos. 6,335,315, 5,674,832, 5,759,990, 5,877,145, 5,574,179; 5,562,849, 5,545,350, 5,545,340, 5,411,671, 5,403,499, 5,288,417, 4,767,547, 4,424,134. Shampoo and conditioners that can employ the present invention include U.S. Pat. Nos. 6,162,423, 5,968,286, 5,935,561, 5,932,203, 5,837,661, 5,776,443, 5,756,436, 5,661,118, 5,618,523, 5,275,755, 5,085,857, 4,673,568, 4,387,090 and 4,705,681.

In certain embodiments, the final consumer product or composition may be in the form of an oil, a gel, a solid stick, a lotion, a cream, a milk, an aerosol, a spray, a powder, a foam, a shampoo, a body wash, a soap bar, a hair conditioner, a lacquer or a make-up.

Consumer product compositions according to the invention may also include vitamins and derivatives thereof, sunscreens, preservatives, chelators and sequestrants and aesthetic agents such as dyes, mica, titanium dioxide, ethylene glycol distearate (EGDS).

The invention is described in greater detail by the following non-limiting examples.

EXAMPLE 1

Cubic Liquid Crystalline Phase

Oil-continuous liquid crystalline phase formulations (#1 and #2), which form cubic liquid crystalline phases, were prepared by adding a polyurea capsule slurry, which contains water necessary for the phase to form in-situ, to the surfactant mixture (Table 1).

A mixture of 75% tetraethoxy nonyl phenol and 25% sodium benzene alkyl sulphonate were mixed and heated to 50° C. To 100 grams of this surfactant mixture was added 43 grams of capsule slurry containing 50% water. The resultant preparation, a cubic liquid-crystalline phase with polyurea capsules dispersed and entrapped in the phase was obtained. One gram of this phase was added to shampoo base and mixed. The fragrance released from capsules was measured after use and was found to be higher than from a shampoo containing an equivalent amount of capsule slurry without the surfactant phase.

TABLE 1

| Form. | Surfactant 1 | Surfactant 2 | Co-surfactant | |
|---|---|---|---|---|
| #1* | 20% sodium benzene alkyl sulphonate | 46.5% tetraethoxy nonyl phenol | 3.5% dodecanol | 30% polyurea capsule slurry (50% water) |
| #2 | 39% Dioleoyl ammonium methosulfate | 24% Sodium bis-tridecyl sulphosuccinate | 7% rhodinol | 30% polyurea capsule slurry (50% water) |

*This formulation is particularly suited for a shower gel or shampoo base.

EXAMPLE 2

Inverse Hexagonal Phase

Oil-continuous liquid crystalline phase formulations (#3, #4), which form an inverse hexagonal phase, were prepared with polyurea capsule slurry supplying the water necessary to form the phase and entrap the capsules (Table 2). The resultant inverse hexagonal phase containing the capsules was added to a hair conditioner base.

TABLE 2

| Form. | Surfactant 1 | Surfactant 2 | Fragrance oil/co-surfactant | Polyurea capsule slurry (%) |
|---|---|---|---|---|
| #3 | 43% Sodium dioctylsulfo-succinate | 7% methyl bis (Soya amidoethyl) hydroxyethlyl ammonium methyl sulfate | 20% | 30% |
| #4 | 52.5% methyl bis (Soya amidoethyl) hydroxyethlyl ammonium methyl sulfate | | 17.5% oleic acid | 30% |

In this example, the oil-surfactant mixture absorbed water upon introduction of the water containing capsule slurry to form the oil continuous lyotropic liquid crystal. The resultant preparation was added to hair conditioner. After use and upon combing, more fragrance was released above the hair than from a control containing the same amount of capsule in the absence of the inverse hexagonal phase.

EXAMPLE 3

Performance of Polyurea Microcapsules in Shampoo and Hair Conditioner

A shampoo application procedure was used to test the performance of polyurea microcapsules. Two bundles of hair (4 strands of hair/bundle) were wet under water and lightly squeezed to remove excess water. The hair was placed onto a balance and 2 grams of shampoo were directly applied onto the wet hair (1 gram of product/bundle). The hair was lathered between palms 10× clockwise and counterclockwise, keeping the wax part of the swatches between two fingers so that the wax was not spread over the surface of the hair. The hair swatches were allowed to stand for 15 seconds and subsequently rinsed under a stream (1 gallon/minute) of water (100° F./38° C.) for 45 seconds. The hair was gently squeezed to remove excess water and hung overnight to dry.

A hair conditioner application procedure was also used to test the performance of polyurea microcapsules. Two bundles of hair (4 strands of hair/bundle) were wet under water and lightly squeezed to remove excess water. The hair was placed onto a balance and 2 grams of unfragranced shampoo were directly applied onto the wet hair (1 gram of product/bundle). The hair was lathered between palms 10× clockwise and counterclockwise, keeping the wax part of the swatches between two fingers so that the wax was not spread over the surface of the hair. The hair swatches were allowed to stand for 15 seconds and subsequently rinsed under a stream of water (1 gallon/minute; 100° F./38° C.) for seconds. The procedure was repeated with hair conditioner, the hair was gently squeezed to remove excess water and hung overnight to dry.

Figure 2:
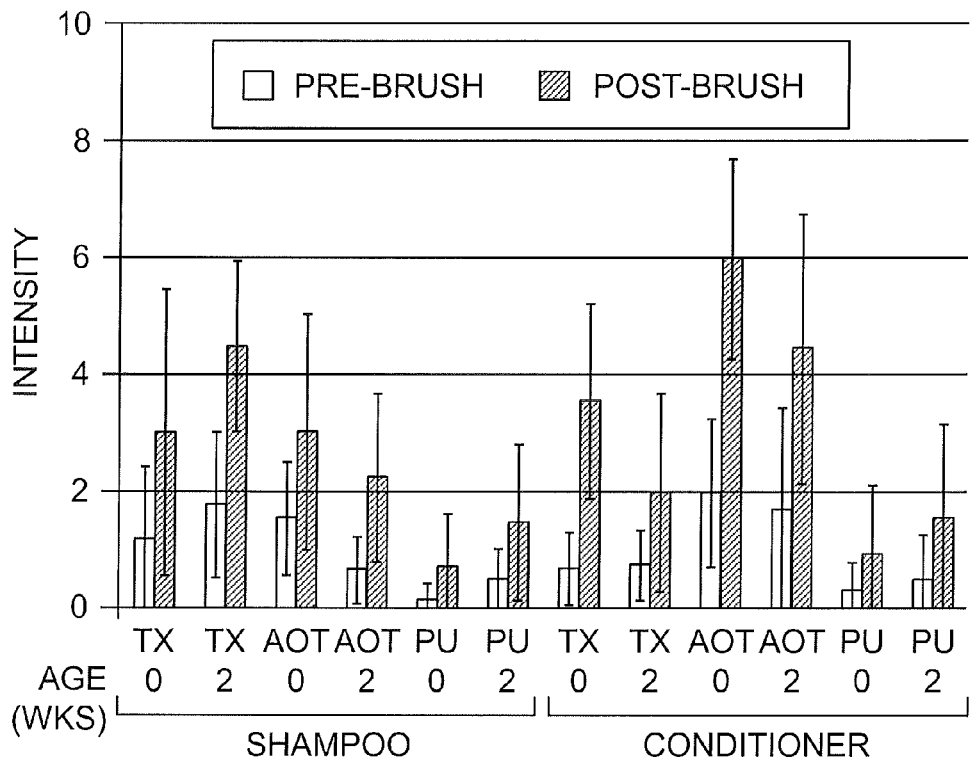
FIG. 2 shows the intensity of fragrance in vapor above hair washed with products (shampoo and condition) containing fragrance microcapsules (polyurea (PU) microcapsules) alone or fragrance microcapsules in TRITON X100 (TX) or lyotropic liquid crystalline phase composed of sodium dioctylsulfo-succinate (AOT). Fragrance microcapsule preparations were used fresh (0) or after storage for 2 weeks (2). N=13.

Increased levels of fragrance in vapor above hair washed were achieved with products containing fragrance microcapsules in lyotropic liquid crystalline phases (FIG. 2).

EXAMPLE 4

Performance Enhancement of Polyurea Microcapsules in Liquid Detergent

Figure 3:
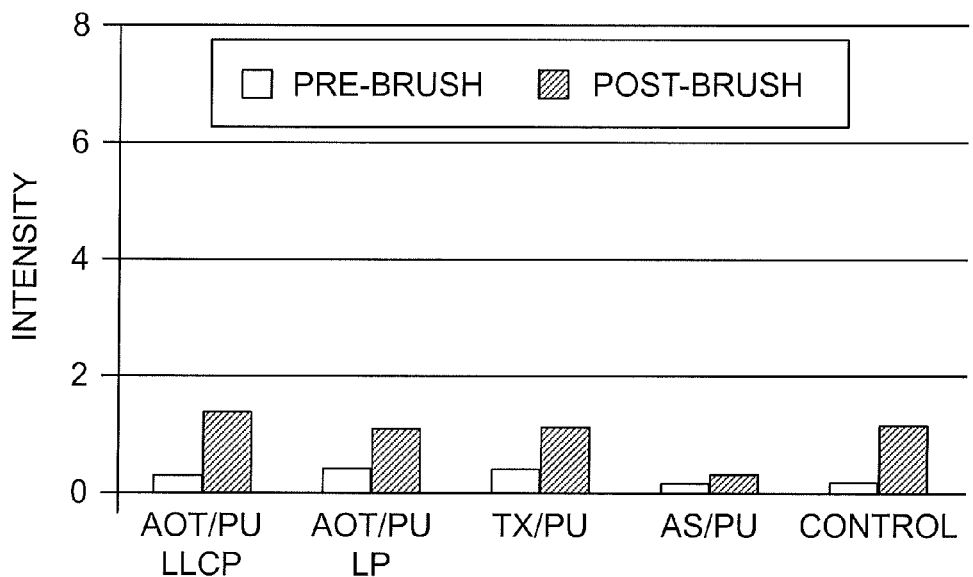
FIG. 3 shows the intensity of fragrance achieved via polyurea (PU) microcapsules dispersed in a lyotropic liquid crystalline phase (LLCP; sodium dioctylsulfo-succinate (AOT)), a lamellar phase (LP; AOT), TRITON X100 (TX), or ACCOSOFT (AS) and incorporated into a liquid detergent, as compared to microcapsules dispersed in the neat liquid detergent (control).

A liquid detergent application procedure was used to test the performance of polyurea microcapsules. The results of this analysis are presented in FIG. 3. This, analysis indicated that polyurea microcapsules dispersed in an organized inverse hexagonal lyotropic liquid crystalline surfactant phase outperformed polyurea microcapsules dispersed in neat liquid detergent.

What is claimed is:

1. A composition comprising fragrance containing capsules dispersed into a lyotropic liquid crystalline surfactant phase, wherein the surfactant phase is an oil-continuous liquid crystalline phase comprising an anionic surfactant and a cationic surfactant, the anionic surfactant is sodium bis-tridecyl sulphosuccinate, and the cationic surfactant is dioleoyl ammonium methosulfate.

2. A composition comprising fragrance containing capsules dispersed into a lyotropic liquid crystalline surfactant phase, wherein the surfactant phase is an oil-continuous liquid crystalline phase comprising an anionic surfactant and a cationic surfactant, the anionic surfactant is sodium dioctyl sulfosuccinate, and the cationic surfactant is methyl bis (Soya amidoethyl) hydroxyethlyl ammonium methyl sulfate.

3. A composition comprising fragrance containing capsules dispersed into a lyotropic liquid crystalline surfactant phase, wherein the surfactant phase is an oil-continuous liquid crystalline phase comprising an anionic surfactant and a cationic surfactant, the anionic surfactant is sodium dioctyl sulfosuccinate, and the cationic surfactant is dipalmityl ammonium methosulfate.

4. The composition of claim 1, wherein the capsules are microcapsules, microparticles, nanoparticles, liposomes, vesicles, spores or a combination thereof.

5. The composition of claim 4, wherein the microcapsules comprise urea-formaldehyde, melamine-formaldehyde, phenolic-formaldehyde, urea-glutaraldehyde, melamine-glutaraldehyde, phenolic-glutaraldehyde, polyurea, polyurethane, silica or a silica-derived material, or combinations thereof.

6. The composition of claim 4, wherein the microcapsules are acrylate-based hydrogel core-shell capsules, polyurea/polyurethane-acrylic hybrid core-shell capsules, or polyamide and polyester-based capsules.

7. The composition of claim 4, wherein the microcapsules are physically or chemically coated with a polymer that facilitates incorporation of the microcapsules into the surfactant phase.

8. The composition of claim 4, wherein the microcapsules or nanoparticles comprise polyethylene, poly vinyl acetate, ethylene-vinyl acetate copolymers, polyacrylate, polyurethane, polyurea, formaldehyde resin, polyester, or polyamide.

9. The composition of claim 4, wherein the spores are plant spores optionally coated with a polymer.

10. The composition of claim 4, wherein the vesicles are polymersomes.

11. A consumer product comprising the composition of claim 1.

12. The consumer product of claim 11, wherein said product is prepared by
(a) mixing a non-organized surfactant phase with a dispersion comprising fragrance containing capsules, and
(b) adding said mixture to a consumer product thereby forming a consumer product with fragrance containing capsules dispersed into a lyotropic liquid crystalline surfactant phase.

13. The consumer product of claim 11, wherein said product is prepared by mixing a consumer product with fragrance containing capsules dispersed into a lyotropic liquid crystalline surfactant phase.

14. The consumer product of claim 11, further comprising a cationic or amphoteric polymer, or blend thereof.

15. The composition of claim 2, wherein the capsules are microcapsules, microparticles, nanoparticles, liposomes, vesicles, spores or a combination thereof.

16. The composition of claim 15, wherein the microcapsules comprise urea-formaldehyde, melamine-formaldehyde, phenolic-formaldehyde, urea-glutaraldehyde, melamine-glutaraldehyde, phenolic-glutaraldehyde, polyurea, polyurethane, silica or a silica-derived material, or combinations thereof.

17. The composition of claim 15, wherein the microcapsules are acrylate-based hydrogel core-shell capsules, polyurea/polyurethane-acrylic hybrid core-shell capsules, or polyamide and polyester-based capsules.

18. The composition of claim 15, wherein the microcapsules are physically or chemically coated with a polymer that facilitates incorporation of the microcapsules into the surfactant phase.

19. The composition of claim 15, wherein the microcapsules or nanoparticles comprise polyethylene, poly vinyl acetate, ethylene-vinyl acetate copolymers, polyacrylate, polyurethane, polyurea, formaldehyde resin, polyester, or polyamide.

20. The composition of claim 15, wherein the spores are plant spores optionally coated with a polymer.

21. The composition of claim 15, wherein the vesicles are polymersomes.

22. A consumer product comprising the composition of claim 2.

23. The consumer product of claim 22, wherein said product is prepared by
(a) mixing a non-organized surfactant phase with a dispersion comprising fragrance containing capsules, and
(b) adding said mixture to a consumer product thereby forming a consumer product with fragrance containing capsules dispersed into a lyotropic liquid crystalline surfactant phase.

24. The consumer product of claim 22, wherein said product is prepared by mixing a consumer product with fragrance containing capsules dispersed into a lyotropic liquid crystalline surfactant phase.

25. The consumer product of claim 22, further comprising a cationic or amphoteric polymer, or blend thereof.

26. The composition of claim 3, wherein the capsules are microcapsules, microparticles, nanoparticles, liposomes, vesicles, spores or a combination thereof.

27. The composition of claim 26, wherein the microcapsules comprise urea-formaldehyde, melamine-formaldehyde, phenolic-formaldehyde, urea-glutaraldehyde, melamine-glutaraldehyde, phenolic-glutaraldehyde, polyurea, polyurethane, silica or a silica-derived material, or combinations thereof.

28. The composition of claim 26, wherein the microcapsules are acrylate-based hydrogel core-shell capsules, polyurea/polyurethane-acrylic hybrid core-shell capsules, or polyamide and polyester-based capsules.

29. The composition of claim 26, wherein the microcapsules are physically or chemically coated with a polymer that facilitates incorporation of the microcapsules into the surfactant phase.

30. The composition of claim 26, wherein the microcapsules or nanoparticles comprise polyethylene, poly vinyl acetate, ethylene-vinyl acetate copolymers, polyacrylate, polyurethane, polyurea, formaldehyde resin, polyester, or polyamide.

31. The composition of claim 26, wherein the spores are plant spores optionally coated with a polymer.

32. The composition of claim 26, wherein the vesicles are polymersomes.

33. A consumer product comprising the composition of claim 3.

34. The consumer product of claim 33, wherein said product is prepared by
   (a) mixing a non-organized surfactant phase with a dispersion comprising fragrance containing capsules, and
   (b) adding said mixture to a consumer product thereby forming a consumer product with fragrance containing capsules dispersed into a lyotropic liquid crystalline surfactant phase.

35. The consumer product of claim 33, wherein said product is prepared by mixing a consumer product with fragrance containing capsules dispersed into a lyotropic liquid crystalline surfactant phase.

36. The consumer product of claim 33, further comprising a cationic or amphoteric polymer, or blend thereof.

* * * * *